US00PP12657P2

(12) United States Plant Patent
Pouw

(10) Patent No.: US PP12,657 P2
(45) Date of Patent: May 28, 2002

(54) MINIATURE ROSE PLANT NAMED 'RUIOVAT'

(75) Inventor: Antonius A. Pouw, De Kwakel (NL)

(73) Assignee: De Ruiter's Nieuwe Rozen B.V., De Kwakel (NL)

( * ) Notice: Subject to any disclaimer, the term of this patent is extended or adjusted under 35 U.S.C. 154(b) by 0 days.

(21) Appl. No.: 09/480,597

(22) Filed: Jan. 10, 2000

(51) Int. Cl.[7] ..... A01H 5/00
(52) U.S. Cl. ..... Plt./116
(58) Field of Search ..... Plt./116, 118, 119, Plt./120, 121, 122

(56) References Cited

PUBLICATIONS

UPOV–ROM GTITM Computer Database, 2000/06, GTI Jouve Retrieval Software, citation for 'Ruiovat'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinctive cultivar of miniature rose plant named 'Ruiovat', characterized by its outwardly spreading growth habit; rapid growth rate; dark green glossy leaves; very freely flowering; large semi-double light salmon-colored flowers that are fragrant; flowers arranged in large sprays; excellent postproduction longevity; and excellent garden performance.

3 Drawing Sheets

BACKGROUND OF THE INVENTION

The present invention relates to a new and distinct cultivar of the miniature rose class, botanically known as *Rosa hybrida*, and hereinafter referred to by the cultivar name Ruiovat.

The new cultivar is a product of a planned breeding program conducted by the Inventor in Hazerswoude, The Netherlands. The objective of the breeding program was to develop compact pot rose varieties with novel and attractive flower colors and excellent postproduction longevity and garden performance. The new cultivar originated from a cross made by the Inventor of two unnamed proprietary seedlings. The cultivar Ruiovat was discovered and selected by the Inventor as a flowering plant within the progeny of the stated cross in a controlled environment in Hazerswoude, The Netherlands. Plants of the new cultivar differ from plants of the parent selections primarily in flower color.

Asexual reproduction of the new cultivar by cuttings taken at Hazerswoude, The Netherlands, has shown that the unique features of this new miniature rose plant are stable and reproduced true to type in successive generations of asexual reproduction.

SUMMARY OF THE INVENTION

The following traits have been repeatedly observed and are determined to be the unique characteristics of 'Ruiovat'. These characteristics in combination distinguish the new miniature rose plant as a new and distinct cultivar:

1. Outwardly spreading growth habit.
2. Rapid growth rate.
3. Dark green glossy leaves.
4. Very freely flowering.
5. Large semi-double light salmon-colored flowers that are fragrant.
6. Flowers arranged in large sprays.
7. Excellent postproduction longevity.
8. Excellent garden performance.

The new miniature rose plant has not been observed under all possible environmental conditions. The phenotype may vary significantly with variations in environment such as temperature and light level, without, however, any variance in genotype.

BRIEF DESCRIPTION OF PHOTOGRAPHS

The accompanying colored photographs illustrate typical specimens of the vegetative growth and flowers of the new miniature rose plant, showing the colors as true as it is reasonably possible to obtain in colored reproductions of this type. Colors in the photographs may differ slightly from the color values cited in the detailed botanical description which more accurately describe the actual colors of the new miniature rose.

The photograph at the top of the first sheet comprises a top perspective view of a typical plant of the new minature rose plant grown in Hazerswoude, The Netherlands.

The photograph at the bottom of the first sheet comprises a close-up view of a typical flower of the new miniature rose.

The photograph on the second and third sheets comprise details of the new miniature rose plant.

In the photograph on the second page is the apex of a young shoot (1); a leaf with three leaflets (2); a leaf with five leaflets (3); a leaf with seven leaflets (4); a stem without leaves (5); and a flower bud after sepals open (6).

In the photograph on the third page is a flower bud after petals begin to unfurl (7); a flower one-half open (8); a flower fully open (9); the reproductive organs (10,11, 12); and a typical flower spray (13) are shown.

DETAILED BOTANICAL DESCRIPTION

The following observations and measurements describe plants grown in Keller, Tex., in 15-cm containers under conditions which closely approximate commercial production outdoor conditions during the summer and early autumn. Plants were about 15 weeks old.

In the following description, color references are made to The Royal Horticultural Society Colour Chart except where general terms of ordinary dictionary significance are used.

Classification:

*Botanical.*—*Rosa hybrida* cultivar Ruiovat.

*Commercial.*—*Miniature pot rose.*

Parentage:

*Male or pollen parent.*—Unnamed proprietary seedling.

*Female or seed parent.*—Unnamed proprietary seedling.

Propagation:

*Type.*—Terminal or stem cuttings.

*Time to rooting.*—8 to 10 days with soil temperatures of 20° C.

*Root description.*—Propagates easily, roots strong and well-branched.

Plant description:

*Form.*—Outwardly spreading; uniform habit.

*Plant height.*—About 29 cm.

*Plant width.*—About 32 cm.

*Growth habit.*—Vigorous, rapid growth rate. Suitable for 10-cm and larger containers.

*Crop time.*—Time to produce a finished plant in a 10-cm container 20 to 30 cm in height and 15 to 20 cm in width is generally about 10 to 12 weeks depending on average temperature, light level, and cultural practices.

*Stem and lateral branches.*—Branching habit: Freely; branches will potentially form at every node. Diameter of lateral branches, at base: About 5 mm. Internode length: About 1.8 cm. Texture: Glabrous. Color: 144A. Prickles: Length: About 4 mm. Color: Brown.

*Foliage description.*—Leaves arranged alternately, compound with typically five leaflets per leaf, generally symmetrical, abundant, and flat in aspect. Stipules at petiole base; stipules about 7 mm in length. Leaflet length: About 2.1 cm. Leaflet width: About 1.1 cm. Shape: Ovate. Apex: Acute. Base: Obtuse. Margin: Serrate. Texture, both surfaces: Glabrous, leathery. Venation pattern: Pinnate. Petiole length: About 1.5 cm to base of lower leaflet; about 3 cm to base of terminal leaflet. Petiole diameter: About 1 mm. Color: Young foliage, upper surface: Darker than 144A. Young foliage, lower surface: Close to 144B. Mature foliage, upper surface: Close to 147A; reddish, 59A, overtones towards and at margins. Mature foliage, lower surface: Close to 147B. Venation: Upper surface: Close to 59A. Lower surface: Similar to ground color. Petiole: Close to 59A.

Flower description:

*Flower type and habit.*—Large semi-double light salmon flowers. Consistently symmetrical rosette flowers that are flat to cupped in shape. Very freely and continuously flowering. The flowers are borne singly on peduncles and arranged in large sprays with about three flowers per spray. Flowers persistent.

*Flowering season.*—Year-round under greenhouse conditions, optimal flowering from spring through autumn under garden conditions.

*Flower diameter.*—About 5.4 cm.

*Flower depth* (*height* ).—About 1.9 cm.

*Flower longevity on plant.*—About 12 to 14 days.

*Fragrance.*—Sweet, typical of Rosa.

*Flower buds.*—Shape: Ovoid. Length: About 1.2 cm. Diameter: About 1 cm. Color: Close to 39B.

*Petals.*—Quantity: About 18 per flower. Typically about three rows with five petals each. Length, outer petals: About 2.75 cm. Width, outer petals: About 3 cm. Shape: Cordate to rounded. Apex: Roughly rounded. Base: Obtuse. Margin: Entire. Texture: Smooth, velvety. Color: When opening, upper surface: Margin, 50A; center, 16D; base, 9C to 16D. When opening, lower surface: Margin, 50A; center, 16D; base, 9C to 16D. Fully opened, upper surface: Margin, 50A; center, 27D to 50A; base, 16D to 155D; with subsequent development, larger area of 50A. Cooler temperatures and higher light levels increase anthocyanin, area towards margin, close to 53B. Fully opened, lower surface: Margin, 50A; center, 27D; base, 27D to 155D.

*Sepals.*—Quantity: Typically five per flower. Length: About 2.1 cm. Diameter: About 7 mm. Shape: Narrowly ovate. Apex: Sharply pointed. Base: Truncate. Texture: Pubescent, fine white hairs on upper surface. Color: Upper surface; 144A; covered with fine white hairs. Lower surface: 144A.

*Peduncles.*—Strength: Good yet flexible. Aspect: Erect. Length: About 2.6 cm. Color: 144A with reddish, close to 59A, overtones.

*Reproductive organs.*—Stamens: Quantity: About 42 per flower. Anther size: About 1.5 by 1 mm. Anther shape: Bilobate. Anther color: 24A. Pistils: Quantity: About 21 per flower. Style length: About 3 mm. Style color: Close to 5C.

*Seed.*—*Seed production has not been observed.*

Disease resistance: Plants of the new miniature rose have been shown to be resistant to Powdery Mildew.

Temperature tolerance: Plants of the new miniature rose have been shown to tolerate temperatures from 0 to 45° C.

It is claimed:

1. A new and distinct miniature rose plant named 'Ruiovat', as illustrated and described.

* * * * *

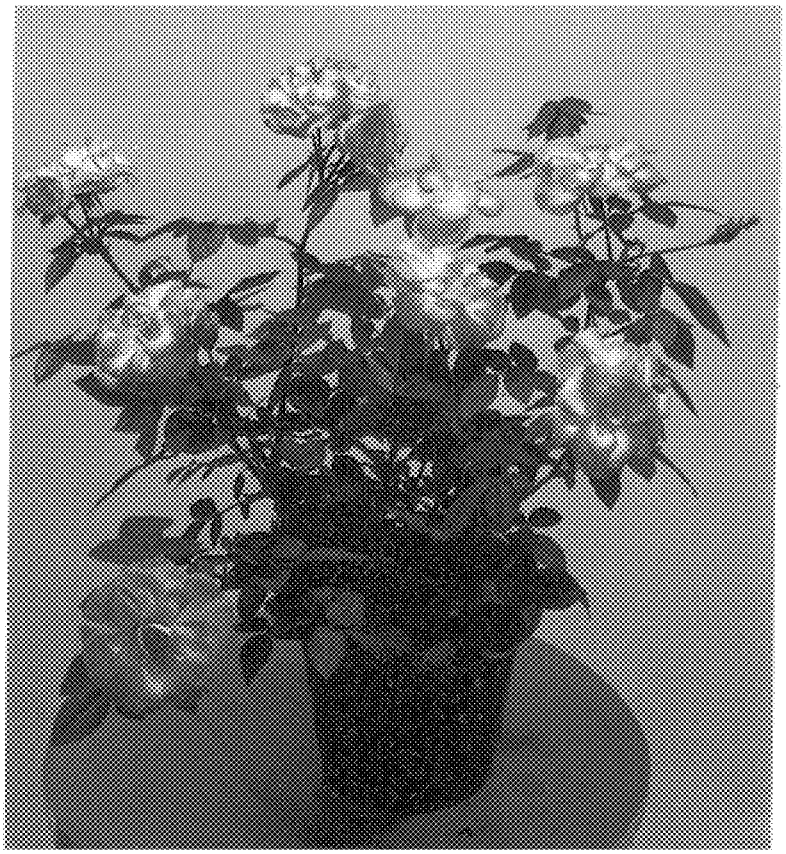
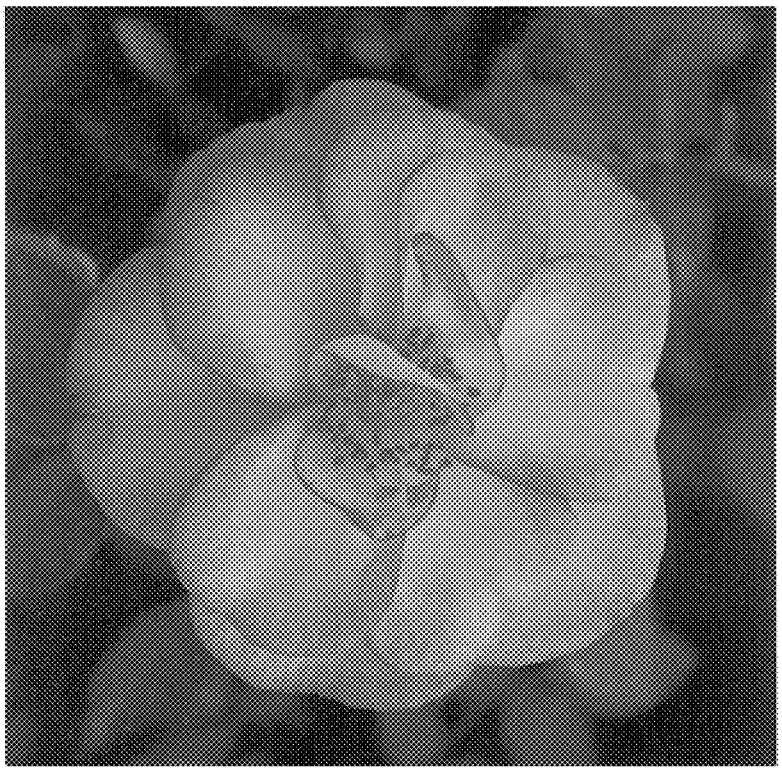

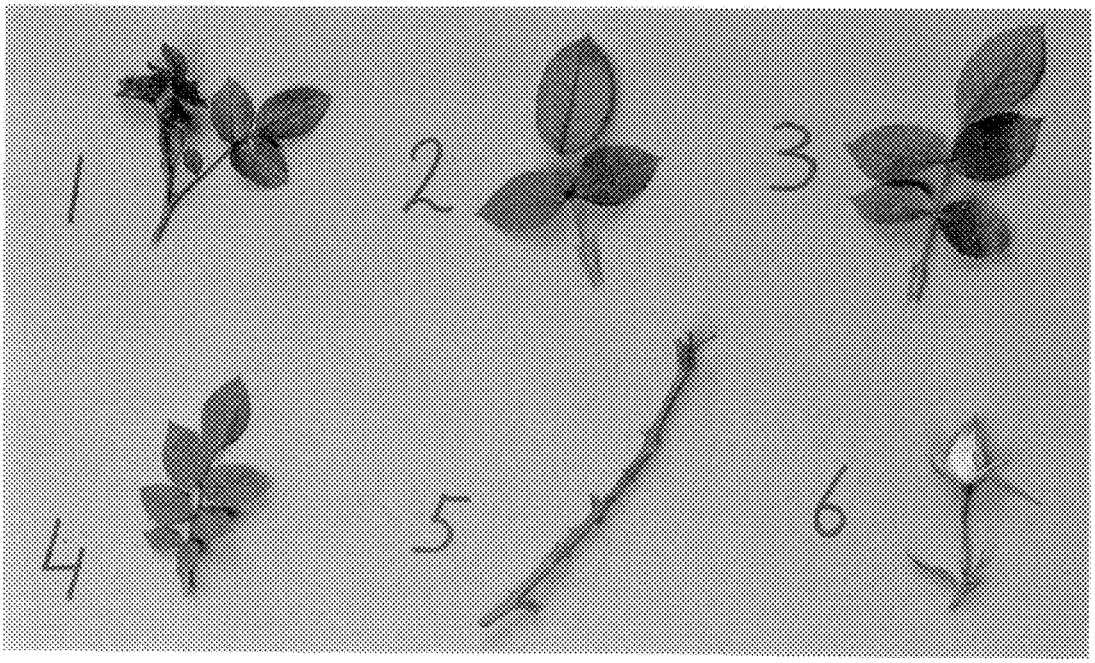
1
2
3
4
5
6

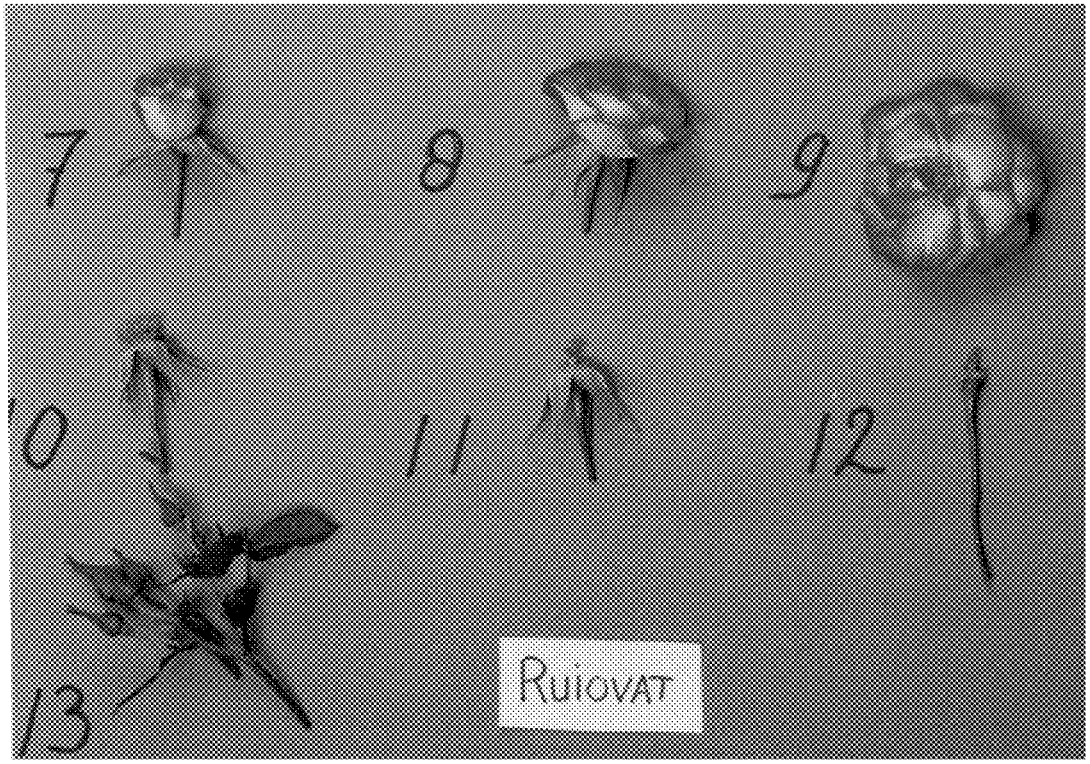
7
8
9
10
11
12
13
RU10VAT